United States Patent [19]
Hofer et al.

[11] 4,211,731
[45] Jul. 8, 1980

[54] FLUORENE PHOSPHONITES AND THIOPHOSPHONITES AS ANTIOXIDANTS FOR ORGANIC MATERIALS

[75] Inventors: Kurt Hofer, Münchenstein; Rudolf Moesch, Stein; Guenther Tscheulin, Frick, all of Switzerland

[73] Assignee: Sandoz Ltd., Basel, Switzerland

[21] Appl. No.: 941,300

[22] Filed: Sep. 11, 1978

[30] Foreign Application Priority Data

Sep. 16, 1977 [CH] Switzerland ............... 11352/77

[51] Int. Cl.² .................... C07F 9/48; C08K 5/53
[52] U.S. Cl. ......................... 260/932; 260/956; 260/45.95 D
[58] Field of Search .................. 260/932, 956

[56] References Cited

U.S. PATENT DOCUMENTS

| | | | |
|---|---|---|---|
| 3,825,629 | 7/1974 | Hofer et al. | 260/932 |
| 3,903,208 | 9/1975 | Hofer et al. | 260/932 |

Primary Examiner—Anton H. Sutto
Attorney, Agent, or Firm—Gerald D. Sharkin; Richard E. Vila; Joseph J. Borovian

[57] ABSTRACT

Fluorene phosphonites and thiophosphonites of the formula,

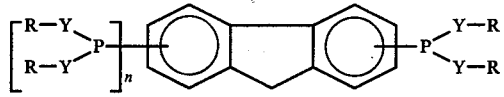

in which each R, independently, is alkyl or optionally substituted phenyl, each Y, independently, is oxygen or sulphur, and n is zero or 1, are useful as antioxidants. Organic materials, which are susceptible to the degradative effects of oxygen, are treated with one or more of such compounds e.g. by incorporation into the body of the organic material, in order to be stabilized against such effects.

5 Claims, No Drawings

FLUORENE PHOSPHONITES AND THIOPHOSPHONITES AS ANTIOXIDANTS FOR ORGANIC MATERIALS

The present invention relates to aryl phosphonites and thiophosphonites, which are useful as antioxidants.

More particularly, the present invention provides compounds of formula I,

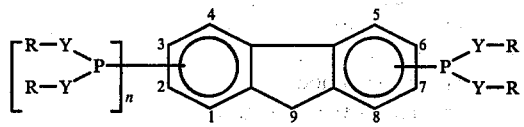

in which
each R, independently, is $(C_{1-18})$alkyl; unsubstituted phenyl; or phenyl substituted with up to four substituents selected from 1 to 3 $(C_{1-9})$alkyl radicals, said alkyl radicals having an aggregate of carbon atoms not exceeding 12, and a halogen atom selected from chlorine and bromine,
each Y, independently, is oxygen or sulphur, and n is zero or 1.

When any R is substituted phenyl, this preferably contains 1 or 2 alkyl substituents, with an aggregate of carbon atoms not exceeding 12. Any halogen substituent in substituted phenyl is preferably chlorine.

When any R is an unsubstituted or substituted phenyl group, this R is preferably R', as hereinafter defined, more preferably a group of formula (a),

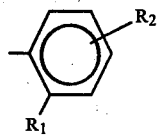

in which
$R_1$ is hydrogen or tertiary-$(C_{4-8})$alkyl,
and $R_2$ is hydrogen or $(C_{1-8})$alkyl.

When this group is attached to oxygen, $R_1$ is preferably tertiary-$(C_{4-8})$alkyl and more preferably tert.-butyl. When the group is attached to sulphur, however, $R_1$ is preferably hydrogen. $R_2$ is preferably in the para-position, and, independently of its position, is preferably methyl or tert.-butyl, more preferably tert.-butyl.

Of all the significances of R, unsubstituted or substituted phenyl is preferred, especially R', as hereinafter defined, more preferably substituted phenyl, especially the substituted phenyl significances of R', and most preferably the substituted phenyl significances of the group of formula (a).

Preferably all R's in the compounds of formula I are the same. All Y's in the compounds of formula I are preferably the same, more preferably oxygen.

n is preferably 1.

When n is zero, the phosphorus atom is preferably attached to the 7-position of the fluorene nucleus, and when n is 1, the phosphorus atoms are preferably attached to the 2- and 7-positions.

A preferred class of compounds of formula I is constituted by the compounds of formula Ia,

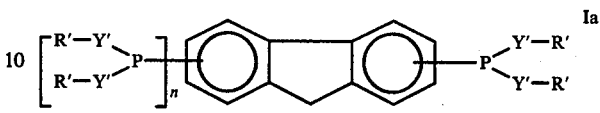

in which
each R', independently, is unsubstituted phenyl or phenyl substituted with 1 or 2 $(C_{1-9})$alkyl radicals, said alkyl radicals having an aggregate of carbon atoms not exceeding 12,
all Y's are the same and are oxygen or sulphur,
and n is zero or 1.

A preferred class of compounds of formula Ia is constituted by the compounds of formula Ib,

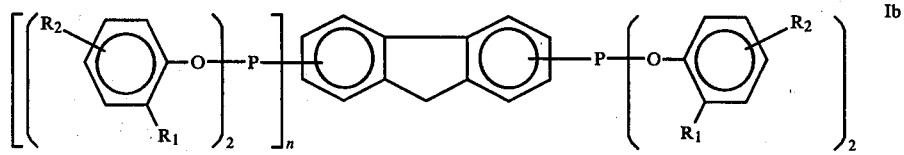

in which all $R_1$'s are the same and are hydrogen or tertiary-$(C_{4-8})$ alkyl,
all $R_2$'s are the same and are hydrogen or $(C_{1-8})$alkyl,
and n is zero or 1,
with the provisos (i) that the aggregate of the carbon atoms in $R_1$ and $R_2$ on each phenyl group does not exceed 12, and (ii) that the $R_2$'s are in equivalent positions on the benzene nuclei.

The present invention further provides a process for the production of the compounds of formula I, as defined above, comprising reacting a compound of formula II,

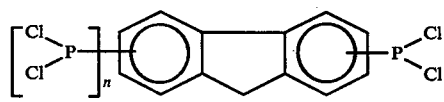

in which n is zero or 1, with a compound or mixture of compounds of formula III, $$R-YH \qquad III$$

in which R and Y are as defined above, in a molar ratio, when n is zero, of 1:at least 2, or when n is 1, of 1:at least 4, respectively.

The intermediates of formula II can be produced in known manner from available starting materials, e.g. by reaction of fluorene with phosphorus trichloride in the presence of a Friedel-Crafts catalyst, e.g. aluminium trichloride.

The intermediates of formula III are either known or can be produced in analogous manner to the known compounds from available starting materials.

The conditions for reacting the compounds of formulae II and III are known from analogous reactions involving the elimination of hydrogen chloride from phosphorus halides and alcohols, phenols, mercaptans or thiophenols. Preferably the elimination reaction is carried out in the presence of an acid binding agent, e.g. a tertiary amine or calcium oxide.

The present invention further provides a method of stabilizing an organic material susceptible to the degradative effects of oxygen against such effects comprising treating said material with a stabilizing-effective amount of one or more compounds of formula I, as defined above. By the term treating, as used herein, is meant either incorporating into the body of the organic material, or surface coating the organic material, e.g. in a manner known per se, of which the former mode of treating is preferred for the preferred organic materials to be treated, i.e. polymeric organic materials.

Suitable organic materials which are stabilized by the method of the present invention include such plastics materials as polyolefins, e.g. polyethylene and polypropylene, polystyrene, polyesters, polymethyl methacrylates, polyphenylene oxides, polyurethanes, polyamides, e.g. nylon, polypropylene oxide, polyacrylonitrile, copolymers and terpolymers of the aforementioned polymers, polypyrrolidone, and such natural materials as natural rubber.

The compounds of the present invention are especially suitable for stabilizing polyethylene, polypropylene, polyesters, polyurethanes, polyamides, polyacrylonitrile, copolymers of styrene and acrylonitrile and of styrene and butadiene, and terpolymers of acrylonitrile, butadiene and styrene (ABS) and of acrylic ester, styrene and acrylonitrile, more particularly polyethylene, polypropylene and (ABS) terpolymers, and most particularly polyethylene and polypropylene.

According to an embodiment of the method of the present invention, the compound of formula I is intimately mixed with a plastics material, e.g. polypropylene, preferably in particulate (granulate) form and preferably in a kneader or other suitable mixing device, to obtain even distribution of the compound in the substrate. The treated material may then be formed into final shape, e.g. by extrusion to form, e.g. films, tubings or fibers.

The polymeric organic materials need not necessarily be in the final polymerized or condensed form before being treated with the compounds of the present invention. Thus, according to a second embodiment of the method of the present invention, particularly suited to the stabilization of polymeric or copolymeric materials, the compound of formula I is mixed with the appropriate monomer or prepolymer and/or precondensate before polymerization or condensation is effected.

The suitable amount of stabilizing compound or compounds of formula I employed in the method of the present invention will naturally depend on several factors, e.g. the mode of application, the particular compound employed and the nature of the organic material to be treated. However, when the compound is incorporated into the body of the organic material, satisfactory results are generally obtained when the amount of compound employed is in the range 0.01 to 5% of the weight of the organic material to be treated. Preferably, however, the amount is in the range 0.05 to 1%, more preferably 0.1 to 0.4%.

The organic materials may also be treated with other additives besides the compounds of formula I to improve their properties, e.g. other stabilizers or costabilizers against the degradative effects of oxygen, heat and/or u.v. light. Particularly preferred additives are distearyl thiodipropionate, tetrakis (methylene-3-dodecylthiopropionate) methane and sterically-hindered phenolic compounds, e.g. 2,2'-methylene-bis(4-methyl or ethyl-6-tert.-butylphenol) or 4,4'-methylene-bis-(2,6-di-tert.-butylphenol). The relative proportion of the compound or compounds of formula I to such additives in the method of the present invention is preferably in the range 1:5 to 5:1, more preferably 1:3 to 4:1, e.g. 1:3, respectively.

The present invention further provides an organic material whenever treated according to the method of the present invention, as well as any suitable composition containing one or more compounds of formula I, as defined above, for use in the method of the present invention. Such compositions, which may be referred to as master batches, preferably comprise 20 to 90% by weight of the compound, or mixture of compounds of formula I, more preferably 40 to 60% by weight, and a part of the substrate to be treated by the method of the present invention. The use of such a master batch in the method avoids the necessity for those practicing the method to initially make up the composition according to recommended ratio specifications before addition to the substrate to be stabilized. The master batch composition is readily worked into or applied onto the main body of the substrate by virtue of the presence of the same substrate in the master batch composition.

In the following Examples, which illustrate the present invention, the parts and percentages are by weight and the temperatures are in degrees Centigrade.

EXAMPLE 1

A mixture of 12.5 parts of fluorene, 26.5 parts of aluminium chloride and 82.5 parts of phosphorus trichloride is heated in a dry atmosphere, under reflux, for 4 hours, after which the excess phosphorus trichloride is removed by distillation in vacuo. To the residual, resinous reaction mixture are added 100 parts of chlorobenzene, followed by 30.7 parts of phosphorus oxychloride, the latter being added dropwise. The mixture is heated to 85° during a period of 10 minutes, and then cooled to 0° and filtered. The collected precipitate is washed with chlorobenzene, and the filtrate and washings are combined.

To the combined filtrate and washings of the previous stage are added 31.6 parts of pyridine, followed, portionwise, by 58,8 parts of 2,4-di-tert.-butylphenol. The mixture is then heated to 80° and maintained at this temperature for 7 hours, after which it is cooled to 0°. After removal of the precipitated salt by filtration, the chlorobenzene solution filtrate is evaporated in vacuo, affording an oily residue which solidifies on cooling. The solid residue is triturated with methanol, and the mixture is filtered. The collected solid is dried, and consists of a pale beige powder, m.p. 142° to 145°. The product has the formula;

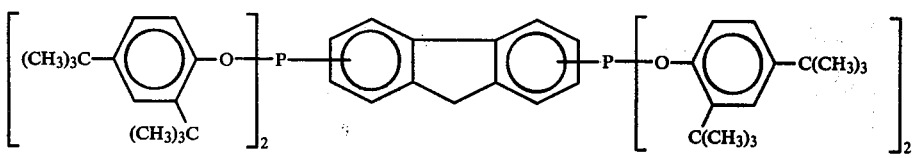

this product being predominantly the 2,7-isomer.

Analysis %

P: found 5.6 calculated 5.9.

EXAMPLES 2 to 7

In an analogous manner to that described in Example 1, the following products of formula I are produced from the appropriate starting materials. The Example 5 product is predominantly the 2-isomer, and the products of the remaining Examples are predominantly the 2,7-isomers.

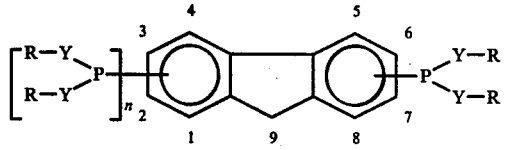

| EXAMPLE NO. | R | Y | n |
|---|---|---|---|
| 2 | —$C_{18}H_{37}$ | O | 1 |
| 3 | —$C_{12}H_{25}$ | S | 1 |
| 4 | ![phenyl with CH3 and C(CH3)3] | O | 1 |
| 5 | ![phenyl with two C(CH3)3] | O | 0 |
| 6 | ![phenyl with C9H19] | O | 1 |
| 7 | ![phenyl with C9H19] | S | 1 |

APPLICATION EXAMPLE

A sample of polypropylene which has been stabilized with 0.1% of the tetra ester of β-(3,5-di-tert.-butyl-4-hydroxyphenyl)propionic acid and pentaerythritol and with 0.1% of calcium stearate ("base-stabilized polypropylene") is mixed with 0.2% of the compound of Example 1 at 70° for 5 minutes using a laboratory rolling mill (Schwabenthan). The resulting polypropylene product is submitted to a melt flow index determination at 2.16 Kp/230° according to the American Standard Test Method (ASTM) D-1238-70.

Unstabilized polypropylene and base-stabilized polypropylene are also submitted to the melt flow index determination. The polypropylene sample stabilized with the compound of Example 1 displays a much lower melt flow index than the unstabilized and base-stabilized polypropylene samples, indicating that the first sample is significantly stabler against oxidation than the unstabilized and base-stabilized samples.

What is claimed is:

1. A compound of formula,

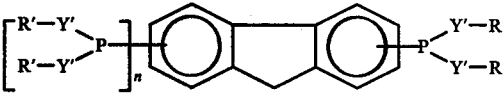

in which
each R, independently, is ($C_{1-18}$)alkyl; unsubstituted phenyl; or phenyl substituted by 1 to 4 substituents selected from ($C_{1-9}$)alkyl, chloro and bromo, with the provisos that: (1) the maximum number of alkyl substituents is three, said alkyl substituents having an aggregate of carbon atoms not exceeding 12; and (2) the maximum number of substituents selected from chloro and bromo is one;
each Y, independently, is oxygen or sulfur; and
n is 0 or 1.

2. A compound according to claim 1, of formula,

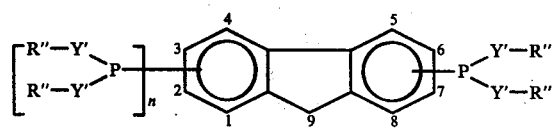

in which
each R', independently, is unsubstituted phenyl; or phenyl substituted by 1 or 2 ($C_{1-9}$)alkyl groups, said alkyl groups having an aggregate of carbon atoms not exceeding 12;
all Y"s are the same and are oxygen or sulfur; and
n is 0 or 1.

3. A compound according to claim 1, of formula, in which
all R'''s are the same and are ($C_{12-18}$) alkyl; unsubstituted phenyl; or phenyl substituted by 1 to 3 ($C_{1-9}$)alkyl groups, said alkyl groups having an aggregate of carbon atoms not exceeding 12;
all Y"s are the same and are oxygen or sulfur; and
n is 0 or 1.

4. A compound according to claim 2, of formula,

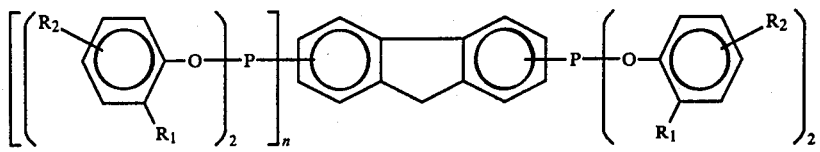
in which
all $R_1$'s are the same and are hydrogen on tertiary—$(C_{4-8})$ alkyl,
all $R_2$'s are the same and are hydrogen or $(C_{1-8})$alkyl,
and n is zero or 1,
with the provisos (i) that the aggregate of the carbon atoms in $R_1$ and $R_2$ on each phenyl group does not exceed 12, and (ii) that the $R_2$'s are in equivalent positions on the benzene nuclei.
5. A compound according to claim 4, of formula,
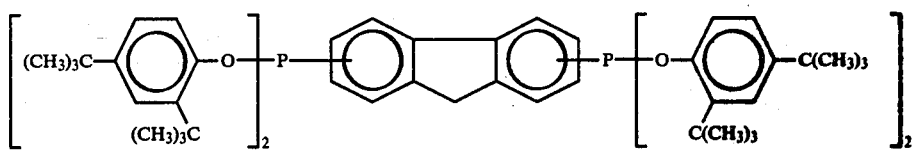

UNITED STATES PATENT AND TRADEMARK OFFICE
CERTIFICATE OF CORRECTION

PATENT NO. : 4,211,731
DATED : July 8, 1980
INVENTOR(S) : Kurt Hofer/Rudolf Moesch/Guenther Tscheulin It is certified that error appears in the above—identified patent and that said Letters Patent is hereby corrected as shown below:

Column 2, line 19; delete "Y's" and insert in its place --Y''s--.

Signed and Sealed this

Eighteenth Day of August 1981

[SEAL]

*Attest:*

*Attesting Officer*

GERALD J. MOSSINGHOFF

*Commissioner of Patents and Trademarks*